Oct. 4, 1966 T. A. CAMPAGNE Plant Pat. 2,674
PLUM
Filed July 27, 1965
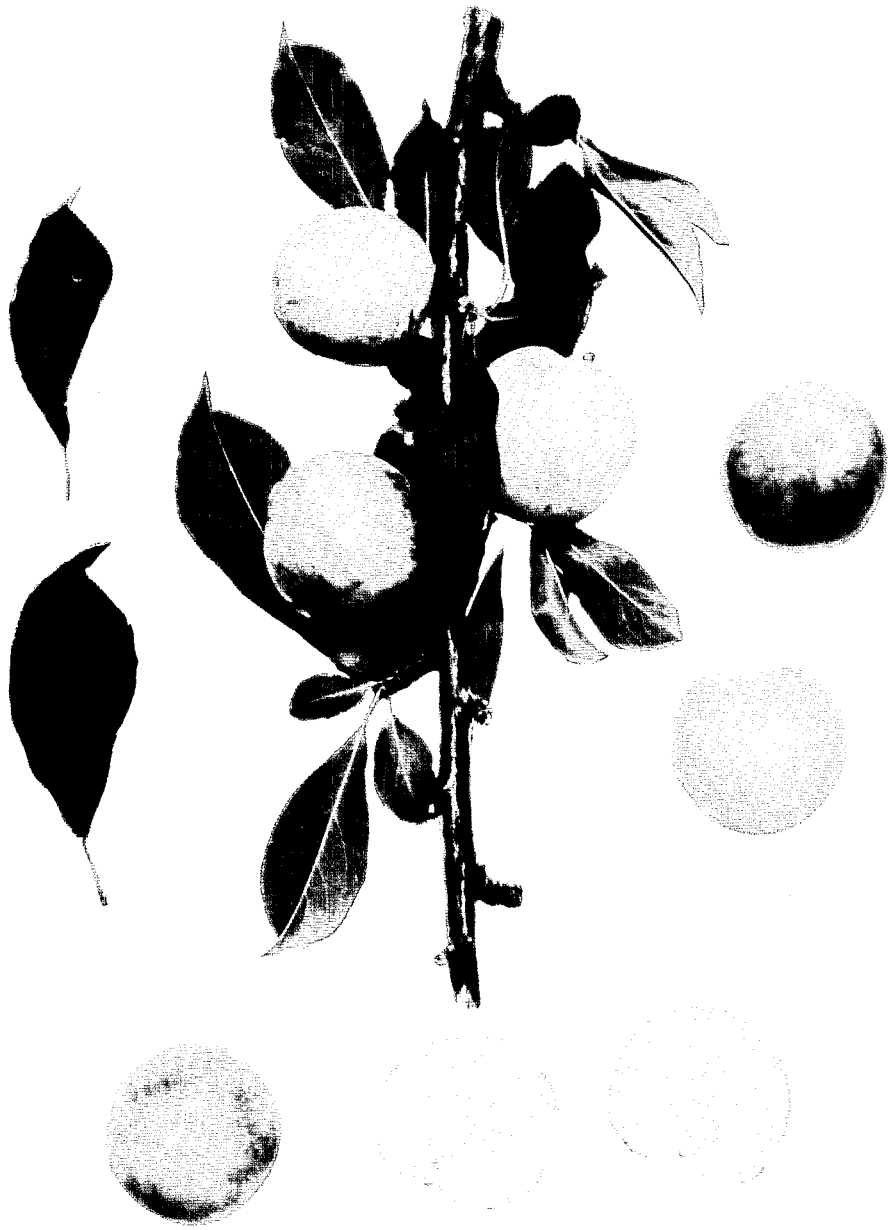
THOMAS A. CAMPAGNE
INVENTOR
Virgil S. Grand
ATTORNEY United States Patent Office Plant Pat. 2,674
Patented Oct. 4, 1966

2,674
PLUM

Thomas A. Campagne, 16339 E. Johnson,
Kingsburg, Calif.

Filed July 27, 1965, Ser. No. 475,301
1 Claim. (Cl. Plt.—38)

This invention relates to a new and distinct variety of plum tree. For many years, applicant has maintained an orchard of Santa Rosa plum trees (unpatented) on his ranch near Fresno, California. Several years ago applicant noticed that one of the trees in the orchard had a different limb on it. The leaves and blossoms came on the limb earlier than on the other limbs, or the other trees in the orchard. Evenutally the limb budded and produced fruit which came on earlier than the fruit from other limbs on the tree or on other trees in the orchard. The fruit was of excellent shape, color and quality.

Subsequently, applicant grafted June buds from the limb on other Santa Rosa trees having Mariana root stock (unpatented). The grafts grew well and yielded about half a dozen fruit two years later. The following year the graft produced about five dozen plums which came on earlier than the Santa Rosa plums and were of better color, shape and quality.

Thereafter, applicant grafted 45 trees with scions from the new variety. These grafts were made on six year old Santa Rosa trees of the Mariana root stock variety. No fruit was produced that year or the next year, however, the following year good fruit production was achieved. Again, the plums ripened earlier than the Santa Rosa and were of better shape and color and excellent quality .

The most significant feature of the new variety of plum is its early maturity. The blossom comes very early in March and the fruit is ready for market about mid May. By contrast, the early Santa Rosa is ready for market by mid June and the Burmosa, which is a new variety and apparently unpatented, comes on the market toward the end of May. The new variety bears at least one to two weeks earlier than the Burmosa and three to four weeks earlier than the Santa Rosa in its maturity.

Furthermore, the fruit of the claimed variety has a short strong stem which greatly reduces the drop of fruit from the trees just before harvesting. It is recognized that the Santa Rosa plum has a tendency to drop from the tree because the stem is not strong enough to support the fruit weight. The new variety of plum greatly improves this condition.

In addition, the fruit of the claimed variety forms better than the Santa Rosa. The Santa Rosa has a tendency to "sheep-nose" and form doubles which are undesirable to the market. The fruit of the instant variety is round and apple-shaped and few if any doubles are produced. The fruit of the claimed variety also has good body to withstand shipping and an excellent dark red color and good flavor which make it prime fruit in the market place.

The accompanying drawing shows typical specimens of the fruit and foliage of the claimed new plum tree taken about picking time in May. The colors are as nearly true as is reasonably possible in a color presentation of this type.

The following is a detailed description of the characteristics of the subject plant in accordance with the outline suggested by U. P. Hedrick in his book entitled "Systematic Pomology" published in 1925 and in accordance with the color terminology employed in the dictionary of color by Maerz and Paul, second edition. Where dimensions, sizes, colors or other characteristics, are given, it is to be understood that such characteristics are approximations of averages set forth as accurately as practical.

Tree: The size, figure, and shape of the new plum tree are approximately the same as the Santa Rosa plum tree.

*Productivity.*—Heavier than the Santa Rosa.

*Regularity of bearing.*—Very regular.

*Trunk.*—The diameter in relation to length and surface characteristics of the trunk are approximately the same as the Santa Rosa plum tree.

*Branches.*—Size; similar to Santa Rosa. Surface character; generally slightly smoother than the Santa Rosa, medium to rough on advance growth and smoother on newer growth. Color; newer growth—Plate 14–F–4, advanced growth—Hudson Seal Plate 8–A–9. Lenticels; typical in number and size.

*Leaves.*—Size; similar to Santa Rosa. Length; approximate average 4⅛ inches. Width; approximate average 1⅝ inches. Shape; similar to Santa Rosa. Color; Plate 23–J–9. Marginal Form; similar to Santa Rosa. Petiole; length—¾ of an inch, thickness—1/16 of an inch. Stem glands; number—usually one, arranged on leaf near petiole, size—minute, type—reniform.

Flower buds: Similar to Santa Rosa but slightly greater in number.

Flowers:

*Dates of bloom.*—Three to four weeks earlier than early Santa Rosa.

*Size and color.*—Similar in size to early Santa Rosa but light pink in color.

Fruit:

*Maturity.*—Matures about three to four weeks earlier than early Santa Rosa; that is, the new variety matures between about May 5 and May 20.

*Size.*—Similar to early Santa Rosa where unthinned.

*Uniformity.*—Very uniform. Axial diameter; appproximately 2 inches. Transverse diameter—in the suture plane; approximately 2 inches. Transverse diameter at right angles to the suture plane; approximatey 2 inches.

*Form.*—Generally uniform and spherical, apple-like. Symmetry; symmetrical. Suture; 3¼ inches long, having a typical position extended from within the cavity to and terminating usually precisely at the axis, and being visible, although essentially a dark line on the surface of the fruit. Stem cavity; deep and nearly conical. Base; rounded and symmetrically conically descending into cavity. Apex; rounded to flat. Stem length; ¼ to ⅜ of an inch. Stem diameter; 1/16 of an inch. Skin; characteristically very smooth in texture and slightly stronger than the Santa Rosa. Color; deeper red than the early Santa Rosa and approximately carbuncle Plate 8–L–7 and possessing better than characteristic bloom.

*Flesh.*—Color; deep yellow like Ta-Ming Plate 10–L–6. Surface of pit cavity; medium. Color of pit well; approximately Marigold Plate 10–L–10 although darkening slightly by virtue of its attachment to the stone. Juice; similar to Santa Rosa. Flavor; more delicate than Santa Rosa. Aroma; slight but characteristically like Santa Rosa. Texture; similar to Santa Rosa. Fibers; typical. Ripening quality; ripens evenly. Eating quality; excellent.

*Stone.*—Free stone, without fibers. Size: major axis length of 1 inch, by minor axis length of ¾ of an inch in the suture plane, by minor axis length of ⅜ of an inch at right angles to the suture plane. Form; elliptic, apex pointed, base blunt, slightly furrowed in the base and along the edges and otherwise rough. Color; deep yellow like Saratoga Plate 11–J–8. No splitting tendency observed.

*Use.*—Eating, shipping and canning.

*Keeping quality.*—Very good. The fruit can be stored under refrigeration for three to four weeks prior to shipment to eastern markets.

*Shipping quality.*—Particularly good.

Growth characteristics: Very vigorous like Santa Rosa—good resistance to disease; reasonable water requirements—approximately three years from planting to fruit.

The new variety of plum tree, as described above, is described as it exists under the ecological conditions prevaling in the Central San Joaquin Valley. Normal variations can be expected under different environmental conditions.

Having thus described a new plum tree what is claimed is:

A new and distinct variety of plum tree substantially as illustrated and described and being characterized by its early maturity, approximately three weeks earlier than the unpatented early Santa Rosa, by fruit which is better formed than the Santa Rosa, better flavored than the Santa Rosa, and does not drop from the tree during ripening as extensively as the early Santa Rosa; and by fruit skin which is somewhat darker red in color and more resistant to bruising than the early Santa Rosa.

No references cited.

ANTONIO F. GUIDA, *Acting Primary Examiner.*

R. E. BAGWILL, *Assistant Examiner.*